United States Patent
Jeon et al.

(10) Patent No.: US 11,377,540 B2
(45) Date of Patent: Jul. 5, 2022

(54) COUPLING AGENT FOR RUBBER COMPOSITION AND RUBBER COMPOSITION FOR TIRE COMPRISING THE SAME

(71) Applicant: OCI COMPANY LTD., Seoul (KR)

(72) Inventors: Yong-Jin Jeon, Seongnam-si (KR); Jae-Seok Lee, Seongnam-si (KR); Seock-Kyeong Choi, Seongnam-si (KR)

(73) Assignee: OCI COMPANY LTD., Seoul (KR)

( * ) Notice: Subject to any disclaimer, the term of this patent is extended or adjusted under 35 U.S.C. 154(b) by 491 days.

(21) Appl. No.: 16/582,291

(22) Filed: Sep. 25, 2019

(65) Prior Publication Data
US 2020/0102447 A1  Apr. 2, 2020

(30) Foreign Application Priority Data
Sep. 27, 2018  (KR) .................. 10-2018-0115197

(51) Int. Cl.
*C08L 9/00* (2006.01)
*C07D 307/20* (2006.01)
*C08K 5/06* (2006.01)
*C08K 5/1535* (2006.01)
*C08K 3/04* (2006.01)
*C08L 7/00* (2006.01)

(52) U.S. Cl.
CPC .............. *C08L 9/00* (2013.01); *C07D 307/20* (2013.01); *C08K 3/04* (2013.01); *C08K 5/06* (2013.01); *C08K 5/1535* (2013.01); *C08L 7/00* (2013.01); *C08L 2312/02* (2013.01)

(58) Field of Classification Search
CPC .......... C08L 7/00; C08L 9/00; C08L 2312/02; C07D 307/20; C08K 5/1535; C08K 3/04; C08K 5/06; Y02T 10/86
See application file for complete search history.

(56) References Cited

U.S. PATENT DOCUMENTS

2017/0267840 A1 * 9/2017 Balnis ..................... C08L 9/06

* cited by examiner

*Primary Examiner* — Angela C Scott
(74) *Attorney, Agent, or Firm* — Hauptman Ham, LLP

(57) ABSTRACT

Disclosed are a coupling agent for a rubber composition and a rubber composition for a tire containing the same. The rubber composition according to the present disclosure contains a coupling agent that may induce interactions between a rubber as a raw material and carbon black, thereby improving dispersibility of the carbon black in the rubber composition. Thus, a tire with low rolling-resistance and excellent wear resistance may be realized.

7 Claims, No Drawings

COUPLING AGENT FOR RUBBER COMPOSITION AND RUBBER COMPOSITION FOR TIRE COMPRISING THE SAME

CROSS-REFERENCE TO RELATED APPLICATIONS

This application claims the priority of Korean Patent Application No. 10-2018-0115197 filed on Sep. 27, 2018, in the Korean Intellectual Property Office, the disclosure of which is hereby incorporated by reference in its entirety.

BACKGROUND

1. Technical Field

The present disclosure relates to a coupling agent for a rubber composition and a rubber composition for a tire containing the same.

2. Description of the Related Art

In recent years, as interest in an environment has increased, demand for fuel consumption reduction for automobiles has increased. Since physical properties of a tire have a great influence on the fuel economy of automobiles, there is a strong demand for a rubber composition suitable for such a purpose.

For example, a rolling-resistance property of a tire tread is determined by characteristics of a tread surface layer in contact with a ground. Due to a frictional force inevitably occurring during a vehicle travels, a lower rolling-resistance may increase the fuel economy of the vehicle.

A rubber composition for forming the tire tread includes carbon black or silica to improve reinforcement and wear resistance.

When carbon black is used as a filler, dispersibility of carbon black in the rubber composition is generally poor. For this reason, carbon black having a large diameter is generally used or a content of the carbon black in the rubber composition is relatively smaller. However, in this case, there is a problem that the wear resistance of the tire tread is not sufficient. In one example, when silica is used as a filler, there is a problem in that the wear resistance improvement effect is generally insufficient compared to the carbon black.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure is to provide a coupling agent for improving dispersibility of carbon black as a filler in a rubber composition for a tire, especially in a rubber composition for preparing a tire tread.

Further, another purpose of the present disclosure is to provide a rubber composition that contains a coupling agent that may induce interaction between a rubber as a raw material and carbon black in a rubber composition to improve dispersibility of carbon black in the rubber composition, such that a tire prepared using the rubber composition according to the present disclosure has low rolling-resistance and excellent wear resistance.

Purposes of the present disclosure are not limited to the above-mentioned purpose. Other purposes and advantages of the present disclosure as not mentioned above may be understood from following descriptions and more clearly understood from embodiments of the present disclosure. Further, it will be readily appreciated that the purposes and advantages of the present disclosure may be realized by features and combinations thereof as disclosed in the claims.

In order to achieve the above technical purpose, according to one aspect of the present disclosure, there is provided a coupling agent for a rubber composition as represented by a following Chemical Formula 1:

[Chemical Formula 1]

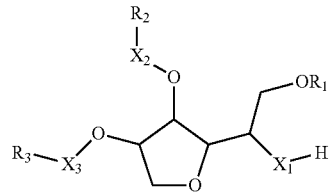

where, each of $X_1$ to $X_3$ independently represents a linking group represented by a following Chemical Formula 2:

[Chemical Formula 2]

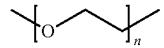

where n denotes an integer of 1 to 10, and each of $R_1$ to $R_3$ independently represents a fatty acid having 6 or greater carbon atoms.

Further, according to another aspect of the present disclosure, there is provided a rubber composition for a tire which contains a rubber as a raw material, carbon black and the coupling agent represented by the above Chemical Formula 1.

Moreover, according to yet another aspect of the present disclosure, a tire prepared using the rubber composition for a tire as defined above is provided.

Effects of the present disclosure are as follows but are not limited thereto.

The coupling agent for the rubber composition according to the present disclosure contains a functional group that may interact with each of the rubber as a raw material and carbon black, thereby to promote coupling between the rubber as a raw material and the carbon black, thus to improve dispersibility of the carbon black in the rubber composition.

Further, the rubber composition according to the present disclosure has the coupling agent that promotes the coupling between the rubber as a raw material and the carbon black to allow a tire made of the rubber composition to have low rolling-resistance and excellent wear resistance.

In addition to the effects as described above, specific effects of the present disclosure are described together with specific details for carrying out the present disclosure.

DETAILED DESCRIPTIONS

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims. Descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, a coupling agent for a rubber composition according to the present disclosure will be described in detail.

According to one aspect of the present disclosure, there is provided a coupling agent for a rubber composition as represented by a following Chemical Formula 1:

[Chemical Formula 1]

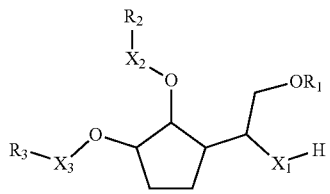

where each of $X_1$ to $X_3$ independently represents an ethylene glycol-based linking group represented by a following Chemical Formula 2, and n is an integer between 1 and 10:

[Chemical Formula 2]

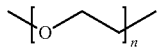

where each of $R_1$ to $R_3$ independently represents a fatty acid having 6 or greater carbon atoms.

In this connection, the fatty acid is a saturated fatty acid ($CH_3(CH_2)_nCO_2H$) in which an aliphatic functional group linked to a carboxyl group is free of an unsaturated bond or an unsaturated fatty acid in which at least one unsaturated bond is present in an aliphatic functional group linked to a carboxyl group.

The saturated fatty acid may include, for example, caprylic acid, capric acid, lauric acid, myristic acid, palmitic acid, stearic acid, arachidic acid, behenic acid, lignoceric acid or cerotic acid.

The unsaturated fatty acid may include, for example, myristoleic acid, palmitoleic acid, sapienic acid, oleic acid, elaidic acid, vaccenic acid, linoleic acid, linoeladidic acid, arachidonic acid, eicosapentaenoic acid, erucic acid or sorbic acid.

Each of the saturated fatty acids and unsaturated fatty acids as listed above may independently be a fatty acid functional group present at each of $R_1$ to $R_3$. The present disclosure is not limited thereto. Although not described herein by way of example, each of saturated or unsaturated fatty acids of other structures and forms may be present at each of $R_1$ to $R_3$.

Further, it should be understood that the unsaturated fatty acid includes cis-trans isomers unless otherwise noted. For example, for the linoleic acid where each of double bonds of carbons #9 and #12 has a cis-configuration, an unsaturated fatty acid in which a double bond of carbon #9 has a trans-configuration and an unsaturated fatty acid in which a double bond of carbon #12 has a trans-configuration may be present (an unsaturated fatty acid in which both of the double bonds of carbons #9 and #12 have a trans-configuration is the linoleic acid).

Further, although not separately represented in the above Chemical Formula, any carbon in an alkyl or alkenyl chain of the saturated fatty acid or unsaturated fatty acid may be substituted with a functional group other than hydrogen (H).

In this connection, the functional group that may be substituted for any carbon in the alkyl or alkenyl chain of the saturated or unsaturated fatty acid may be preferably a hydrophobic functional group to promote hydrophobic interaction between the carbon black and the coupling agent represented by Chemical Formula 1.

The hydrophobic functional group that may be substituted for any carbon in the alkyl or alkenyl chain of the saturated or unsaturated fatty acid may include, for example, $C_1$-$C_{10}$ alkyl, $C_6$-$C_{12}$ cycloalkyl, $C_2$-$C_{10}$ alkenyl, $C_2$-$C_{10}$ alkynyl, $C_6$-$C_{12}$ aryl or aralkyl.

When the hydrophobic functional group is alkenyl or alkynyl, a $sp^2$-hybrid carbon of alkenyl or a sp-hybrid carbon of alkynyl may be directly bonded to carbon black or may be indirectly bound thereto via a $sp^3$-hybrid carbon of alkyl coupled to the $sp^2$-hybrid carbon of alkenyl or the sp-hybrid carbon of alkynyl.

As used herein, "$C_a$-$C_b$" functional group means a functional group having a to b carbon atoms. For example, "$C_a$-$C_b$" alkyl means a saturated aliphatic group including a straight chain alkyl, branched chain alkyl, and the like having a to b carbon atoms. The straight chain or branched chain alkyl has at most 10 carbon atoms (e.g., $C_1$-$C_{10}$ straight chain, $C_3$-$C_{10}$ branched chain), preferably, at most 4, more preferably, at most 3 carbon atoms in a main chain thereof.

Specifically, alkyl may include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl and n-octyl.

As used herein, "cycloalkyl" may be understood as a cyclic structure of alkyl unless otherwise defined.

Non-limiting examples of cycloalkyl include cyclopentyl, cyclohexyl, 1-cyclohexenyl, 3-cyclohexenyl, cycloheptyl and the like.

As used herein, aryl may refer to an unsaturated aromatic ring containing a single ring or multiple rings (preferably 1 to 4 rings) joined together or covalently linked to one another, unless defined otherwise. Non-limiting examples of aryl may include phenyl, biphenyl, o-terphenyl, m-terphenyl, p-terphenyl, 1-naphthyl, 2-naphthyl, 1-anthryl, 2-anthryl, 9-anthryl, 1-phenanthrenyl, 2-phenanthrenyl, 3-phenanthrenyl, 4-phenanthrenyl, 9-phenanthrenyl, 1-pyrenyl, 2-pyrenyl and 4-pyrenyl and the like.

As used herein, "aralkyl" refers to a functional group in which aryl is substituted for a carbon of alkyl and has a general expression of —$(CH_2)_n$Ar. Examples of aralkyl may include benzyl (—$CH_2C_6H_5$) or phenethyl (—$CH_2CH_2C_6H_5$).

The ethylene glycol-based linking group $X_2$ or $X_3$ as represented by the Chemical Formula 2, and the fatty acid may be coupled to each other under an acid catalyst via a following Reaction Formula 1, thereby to form the coupling agent:

[Reaction Formula 1]

$$R\underset{\text{fatty acid}}{\overset{O}{\|}}OH + H\underset{\text{ethylene glycol}}{\left[O\frown\right]_n}O\text{-}R' \xrightarrow{H^+} R\overset{O}{\|}O\left[\frown O\right]_n O\text{-}R'$$

where R of the fatty acid refers to an alkyl or alkenyl chain bonded to a carbon of a carboxyl group of the fatty acid. The coupling agent may hydrophobic-interact with a hydrophobic surface of the carbon black via the alkyl or alkenyl chain of the fatty acid.

In one example, an ethylene glycol repeat unit of the coupling agent is a hydrophilic linking group which may have not only hydrophilic interaction with a hydrophilic functional group on a surface of the rubber as a raw material but also hydrophilic interaction with a hydrophilic functional group on the carbon black surface, thereby to induce a coupling between the rubber as a raw material and the carbon black.

According to another aspect of the present disclosure, a rubber composition for a tire is provided which contains the rubber as a raw material, the carbon black and the coupling agent represented by a following Chemical Formula 1:

[Chemical Formula 1]

$$\begin{array}{c} R_2 \\ | \\ X_2 \\ \end{array} \text{(cyclopentane ring with substituents } OR_1, X_1\text{-H, } R_3\text{-}X_3\text{-O-)}$$

where each of $X_1$ to $X_3$ independently denotes an ethylene glycol-based linking group represented by a following Chemical Formula 2, wherein n is an integer between 1 and 10:

[Chemical Formula 2]

$$\left[O\frown\right]_n$$

In this connection, the coupling agent is preferably contained in 0.5 to 5 parts by weight based on 100 parts by weight of the rubber composition.

When the content of the coupling agent is smaller than 0.5 parts by weight based on 100 parts by weight of the rubber composition, the coupling promoting effect between the raw material rubber and the carbon black using the coupling agent is insignificant. Thus, it may be difficult to achieve sufficient dispersibility of the carbon black in the rubber composition.

To the contrary, when the content of the coupling agent exceeds 5 parts by weight relative to 100 parts by weight of the rubber composition, by-products from excessive coupling agents may increase or dispersibility of the carbon black in rubber composition and dispersibility between the carbon black and rubber as a raw material may decrease.

In this connection, the rubber as a raw material may include at least one selected from isoprene based rubber and diene based rubber.

The isoprene-based rubber may contain, for example, natural rubber such as deproteinized natural rubber and high purity natural rubber or modified natural rubber such as epoxidized natural rubber, hydrogen-added natural rubber and grafted natural rubber.

The diene based rubber may include, for example, styrene-butadiene rubber (SBR), butadiene rubber (BR), isoprene-containing styrene butadiene rubber or nitryl-containing styrene butadiene rubber.

In addition to the above-mentioned rubber as a raw material, neoprene rubber, chlorobutyl rubber or bromobutyl rubber may be used. Further, as the rubber as the raw material, one kind of the raw material rubber may be used alone, but at least two kinds of the above raw material rubbers may be used in combination with each other.

The rubber as the raw material is preferably contained in 20 to 60 parts by weight based on 100 parts by weight of the rubber composition.

When the content of the rubber as a raw material is smaller than 20 parts by weight with respect to 100 parts by weight of the rubber composition, mechanical properties including a tensile strength may decrease. To the contrary, when the content of the rubber as a raw material exceeds 60 parts by weight based on 100 parts by weight of the rubber composition. this may be disadvantageous in terms of reinforcement and mechanical performance of the rubber composition.

As the carbon black, for example, furnace black, acetylene black, thermal black, channel black, or the like may be used.

The carbon black is preferably contained in an amount of 20 to 50 parts by weight based on 100 parts by weight of the rubber composition.

When the carbon black content is smaller than 20 parts by weight with respect to 100 parts by weight of the rubber composition, the mechanical properties including reinforcement may be deteriorated.

To the contrary, when the carbon black content exceeds 50 parts by weight based on 100 parts by weight of the rubber composition, Mooney viscosity, exothermic performance and viscoelastic properties in the rubber composition may be deteriorated.

Further, the rubber composition according to the present disclosure may additionally contain reinforcing agents such as silica, clay or talc.

In addition, the rubber composition according to the present disclosure may further contain additives a vulcanization accelerator such as sulfenamide, an activator for an vulcanization accelerator such as zinc oxide and magnesium oxide, process oils such as naphthenic oil and aromatic oils, dispersants (wax) such as stearic acid, anti-aging agents, antioxidants, antiozonants, peptizing agents, adhesive resins, vulcanization retardants, etc. such that the coupling interaction between the rubber as a raw material and the carbon black via the coupling agent is not deteriorated.

In addition, according to another aspect of the present disclosure, there is provided a tire prepared using the above-described rubber composition for the tire.

For example, using a kneader such as a Banbury mixer or open roll, the above-described rubber composition may be produced into a rubber member for a tire such as a carcass, belt, bead or tread.

Composition of Rubber Composition for Tire

Present Example 1 parts by weight of a natural rubber, 40 parts by weight of 2 types butadiene rubbers, 40 parts by weight of carbon black, 4 parts by weight of zinc oxide, 1 part by weight of stearic acid, 1 part by weight of an anti-aging agent, and 0.8 parts by weight of a compound represented by a following Chemical Formula 1 as the coupling agent are mixed with each other at 160° C. for 1 minute. Then, After discharging the mixture at 165° C., the mixture was subjected to a second mixing process in which 4.5 parts by weight of sulfur and 1.2 parts by weight of vulcanization accelerator were added thereto at 105° C. Thus, a rubber composition for a tire was prepared:

[Chemical Formula 1]

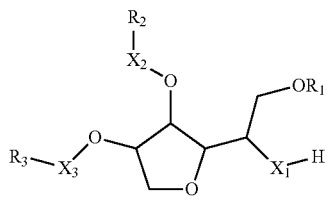

Where each of $X_1$ to $X_3$ independently denotes a linking group represented by a following Chemical Formula 2, wherein n is 1:

[Chemical Formula 2]

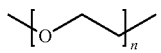

where each of $R_1$ to $R_3$ independently denotes sorbic acid represented by a following Chemical Formula 4:

[Chemical Formula 4]

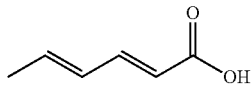

Present Example 2

A rubber composition was prepared in the same manner as in Present Example 1 except that each of $R_1$ to $R_3$ of the coupling agent represented by the Chemical Formula 1 independently denotes oleic acid represented by a following Chemical Formula 5:

[Chemical Formula 5]

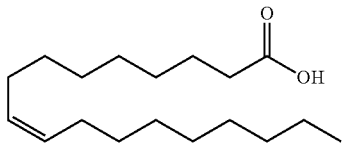

Comparative Example 1

A rubber composition was prepared in the same manner as in Present Example 1 except that no coupling agent was used.

Comparative Example 2

A rubber composition was prepared in the same manner as in Present Example 1 except that bis[(3-thiethoxysilyl)propyl]tetrasulfide (TESPTS) was used as the coupling agent.

Experimental Example 1. Evaluation of Properties of Rubber Composition

The physical properties of the rubber composition prepared according to each of Present and Comparative Examples were evaluated in a following manner.

A. Mooney Viscosity (ML1+4, 100° C.):

Mooney viscosity was measured for a first master batch and rubber composition prepared in each of Present and Comparative Examples according to "ASTM D 1646: Rubber from natural or synthetic sources-Viscosity and Vulcanization characteristics (Mooney viscometer)".

50-ML1+4 (100° C.): 50-M refers to a viscosity number, L indicates use of a large rotor, 1 means that a motor has been warmed for 1 minute before operation thereof, 4 indicates a measuring time, and 100° C. denotes a measuring temperature.

The higher Mooney viscosity means smaller dispersibility of a composition in the first master batch and the rubber composition.

B. Mooney Scorch Time (MST):

Mooney scorch time (MST) was measured for each rubber composition prepared in each embodiment and Comparative Example according to "ASTM D 1646: Rubber-Viscosity, Stress Relaxation, and Pre-Vulcanization characteristics (Mooney Viscometer)".

When the MST is short, scorch may occur quickly. This may reduce the workability of the rubber during tire preparation.

C. Rheometer (MDR):

Rheometer (MDR) was measured for each rubber composition prepared in each of Present and Comparative Examples according to ASTM D1349, ASTM D1556, ASTM D2084, ASTM D4483, ISO 6502, ASTM D 5289.

The longer a t90 time of the rheometer, the lower the productivity during the tire preparation process, particularly in the vulcanization process.

TABLE 1

| Examples | Mooney viscosity (rubber composition) | MST, t5 (138° C.) | Rheometer (150° C.) |
| --- | --- | --- | --- |
| Present Example 1 | 70 | 5.0 | 11.9 |
| Present Example 2 | 71 | 5.1 | 11.6 |
| Comparative Example 1 | 84 | 5.4 | 11.1 |
| Comparative Example 2 | 79 | 5.5 | 11.0 |

Referring to the results of Table 1, in Present Example 1 and Present Example 2, it may be seen that the Mooney viscosity value as measured in the rubber composition is smaller compared to those of Comparative Example 1 and Comparative Example 2. In general, Mooney viscosity tends to decrease when the dispersibility of carbon black in the rubber composition increases.

Further, the Rheometer values of Comparative Example 1 and Comparative Example 2 are slightly faster than those of Present Example 1 and Present Example 2. This may be understood as being due to insufficient dispersibility of carbon black in the rubber composition in Comparative Example 1 and Comparative Example 2.

Experimental Example 2. Evaluation of Properties of Rubber Sheet

A rubber sheet was prepared using a rubber composition prepared according to each of Present and Comparative examples according to ASTM D 3182: Rubber-Preparing Standard Vulcanized Sheet. Physical properties of each rubber sheet prepared using each rubber composition prepared according to each of Present and Comparative Examples were evaluated in a following manner.

A. Hardness:

Rubber hardness was measured according to ASTM D2240 SHORE A2-TYPE rubber hardness measuring method. The hardness of the rubber sheet is considered to be a depth at which a standard sized indentor invades into a surface of the rubber sheet under a predefined pressure.

B. Tensile Stress (M300%) and Elongation:

Tensile stress (M300%) and elongation were measured according to ASTM 412-98a: Standard test methods for Vulcanized rubber and Thermoplastic elastomers-tension.

C. Heat Buildup (HBU):

HBU was measured according to ASTM D623 and ASTM D3182. The larger the HBU value, the smaller the heat generation.

D. Rebound:

The rebound was measured based on ASTM D 2632: Rubber property-resilience vertical rebound, ASTM D 1054: Rubber property-resilience using rebound pendulum. The larger the rebound value, the larger an elastic value, resulting in smaller heat loss.

E. DMA:

The DMA was measured according to ASTM D4065, D4440, D5279. tan δ @60° C. may replace a rolling resistance value. The smaller tan δ @60° C. means better performance.

F. Lambourn Abrasion Loss (LAL):

The LAL was measured according to JIS K6264-93, JIS R6211, JIS R6210, JIS R6111. The smaller Lambourn value means a smaller loss.

Referring to the results of the Table 2, it may be seen that the rubber sheet prepared using each of the rubber compositions according to Present Example 1 and Present Example 2 has a low tan δ60° C. value compared to those of Comparative Example 1 without the coupling agent and Comparative Example 2 with a conventional coupling agent. This may be due to a fact that the improvement in dispersibility of carbon black in the rubber composition may allow reduction of thermal energy loss due to reduction of hysteresis which may occur between carbon black and the rubber.

Further, it may be seen that each of Present Example 1 and Present Example 2 has a high 300% modulus value compared to those Comparative Example 1 and Comparative Example 2. This may be due to a fact that improvement of the cross-linking density of the rubber is realized due to the high dispersibility of the carbon black in the rubber composition.

In other words, the carbon black coupling agent increases the dispersibility of the rubber as a raw material and carbon black in the rubber composition, thereby reducing the amount of the carbon black as crushed by the rubber and thus not dispersed in the rubber, thus resulting in the improvement of the crosslinking density of the rubber.

However, in the Present Example 1 and Present Example 2, the modulus is higher than those of Comparative Example 1 and Comparative Example 2. Thus, the elongation of the Present Example 1 and Present Example 2 tends to have a low value. However, it may be seen that the elongation value is over 500% not to affect the physical properties of the rubber sheet.

Although the present disclosure has been described above with reference to the preferred embodiments of the present disclosure, those skilled in the art will appreciate that various modifications and changes may be made in the present disclosure without departing from the spirit and scope of the present disclosure set forth in the following claims.

What is claimed is:

1. A coupling agent for a rubber composition, wherein the coupling agent is represented by a following Chemical Formula 1:

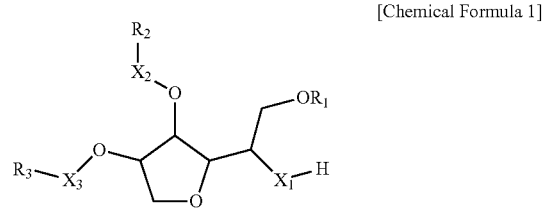

[Chemical Formula 1]

wherein each of $X_1$ to $X_3$ independently represents a linking group represented by a following Chemical Formula 2:

TABLE 2

| Test | Hardness | M300% | Elongation | HBU | Rebound | Tanδ60° C. | Lambourn |
|---|---|---|---|---|---|---|---|
| Present Example 1 | 71 | 151 | 525 | 20 | 48 | 0.09871 | 0.0704 |
| Present Example 2 | 71 | 147 | 537 | 21 | 46 | 0.09879 | 0.0715 |
| Comparative Example 1 | 73 | 137 | 580 | 31 | 42 | 0.09911 | 0.0811 |
| Comparative Example 2 | 71 | 139 | 572 | 32 | 43 | 0.09902 | 0.0725 |

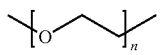

wherein n is an integer between 1 and 10, and each of $R_1$ to $R_3$ independently represents a fatty acid having 6 or greater carbon atoms.

2. The coupling agent of claim 1, wherein each of $R_1$ to $R_3$ independently includes an unsaturated fatty acid containing at least one unsaturated bond.

3. The coupling agent of claim 2, wherein each of $R_1$ to $R_3$ independently includes a fatty acid selected from a group consisting of myristoleic acid, palmitoleic acid, sapienic acid, oleic acid, elaidic acid, vaccenic acid, linoleic acid, linoeladidic acid, arachidonic acid, eicosapentaenoic acid, erucic acid and sorbic acid.

4. A rubber composition for a tires, the composition containing:
a rubber as a raw material;
carbon black; and
a coupling agent represented by a following Chemical Formula 1:

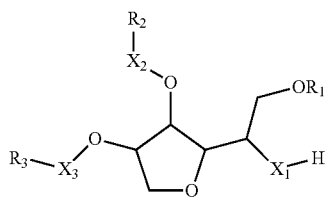

wherein each of $X_1$ to $X_3$ independently represents a linking group represented by a following Chemical Formula 2:

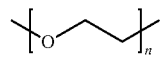

wherein n is an integer between 1 and 10, and each of $R_1$ to $R_3$ independently represents a fatty acid having 6 or greater carbon atoms.

5. The rubber composition of claim 4, wherein the rubber as the raw material includes at least one selected from a group consisting of isoprene based rubber and diene based rubber.

6. The rubber composition of claim 4, wherein each of $R_1$ to $R_3$ independently includes an unsaturated fatty acid containing at least one unsaturated bond.

7. The coupling agent of claim 6, wherein each of $R_1$ to $R_3$ independently includes a fatty acid selected from a group consisting of myristoleic acid, palmitoleic acid, sapienic acid, oleic acid, elaidic acid, vaccenic acid, linoleic acid, linoeladidic acid, arachidonic acid, eicosapentaenoic acid, erucic acid and sorbic acid.

* * * * *